United States Patent
Scheeres

(10) Patent No.: US 10,780,620 B2
(45) Date of Patent: Sep. 22, 2020

(54) APPARATUS AND METHOD FOR VOLUMETRIC REDUCTION OF POLYMERIC MATERIAL

(71) Applicant: Styromelt Limited, Cardiff (GB)

(72) Inventor: David Scheeres, Pembrokeshire (GB)

(73) Assignee: Styromelt Limited, Cardiff (GB)

( * ) Notice: Subject to any disclaimer, the term of this patent is extended or adjusted under 35 U.S.C. 154(b) by 256 days.

(21) Appl. No.: 16/128,250

(22) Filed: Sep. 11, 2018

(65) Prior Publication Data

US 2019/0016033 A1 Jan. 17, 2019

Related U.S. Application Data

(63) Continuation of application No. 14/230,763, filed on Mar. 31, 2014, now abandoned.

(30) Foreign Application Priority Data

Apr. 12, 2013 (GB) .................................. 1306653.5

(51) Int. Cl.
*B29C 48/08* (2019.01)
*B29B 13/02* (2006.01)
(Continued)

(52) U.S. Cl.
CPC ................ *B29C 48/08* (2019.02); *A61L 2/04* (2013.01); *B29B 13/022* (2013.01);
(Continued)

(58) Field of Classification Search
CPC ............ B29C 43/34; B29C 2043/3433; B29C 31/042; B29C 31/02; B29C 48/08;
(Continued)

(56) References Cited

U.S. PATENT DOCUMENTS 4,030,867 A * 6/1977 Everman ................ C11D 13/16
425/144
4,091,967 A * 5/1978 Kinoshita ........... B29B 17/0036
222/238
(Continued)

FOREIGN PATENT DOCUMENTS

GB 2255977 A * 11/1992 ........... B29B 13/022
GB 2255977 A 11/1992
(Continued)

OTHER PUBLICATIONS

Machine Translation of JP 2007001153 A (Year: 2007).*
(Continued)

*Primary Examiner* — Leith S Shafi
(74) *Attorney, Agent, or Firm* — Dinsmore & Shohl LLP

(57) ABSTRACT

The present invention is an apparatus and method for volumetric reduction of polymeric material and in particular synthetic polymeric textile materials. Such materials are typically used in hospital operating rooms and have material memory meaning that they re-expand after compression. Consequently they are difficult to process as waste material. The present invention is a method and apparatus for thermally compacting a polymer comprising a first and second heated surface inclined downwardly towards each other and providing with a passage at their lower ends through which melted polymeric material may pass.

19 Claims, 8 Drawing Sheets

(51) Int. Cl.
    *B29B 17/00*    (2006.01)
    *A61L 2/04*     (2006.01)
    *B29K 23/00*        (2006.01)
    *B29L 31/00*        (2006.01)

(52) U.S. Cl.
    CPC ...... *B29B 17/0047* (2013.01); *B29K 2023/12* (2013.01); *B29L 2031/726* (2013.01); *B29L 2031/753* (2013.01); *Y02W 30/62* (2015.05)

(58) Field of Classification Search
    CPC .............. B29B 13/022; B29B 17/0047; B29B 17/0036; B29B 17/0026; A61L 2/04; A61L 11/00; Y02W 30/62; B29K 2023/12; B29L 2031/726; B29L 2031/753; B09B 3/0075; B02C 19/0075
    See application file for complete search history.

(56) References Cited

U.S. PATENT DOCUMENTS

| | | | |
|---|---|---|---|
| 4,311,555 A | | 1/1982 | Reinhall |
| 5,240,656 A | * | 8/1993 | Scheeres ............... B29B 13/022 |
| | | | 219/421 |
| 5,286,321 A | * | 2/1994 | Fuss ................... B29B 17/0026 |
| | | | 156/497 |
| 5,470,521 A | * | 11/1995 | Wenzel ................. B29B 13/022 |
| | | | 264/321 |
| 5,645,233 A | * | 7/1997 | Chen .................... B02C 18/142 |
| | | | 241/100 |
| 5,645,862 A | | 7/1997 | Sable et al. |
| 2010/0239704 A1 | | 9/2010 | Major |
| 2011/0209615 A1 | | 9/2011 | Ma |

FOREIGN PATENT DOCUMENTS

| | | | | | |
|---|---|---|---|---|---|
| JP | S62205139 A | | 9/1987 | | |
| JP | 2007001153 A | * | 1/2007 | | |
| JP | 2007001153 A | | 1/2007 | | |
| WO | 199107264 A1 | | 5/1991 | | |
| WO | WO-9107264 A1 | * | 5/1991 | ........... | B29B 13/022 |
| WO | 9208590 A1 | | 5/1992 | | |
| WO | WO-9521633 A1 | * | 8/1995 | .............. | A61L 11/00 |
| WO | WO-9623640 A1 | * | 8/1996 | ........... | B09B 3/0075 |
| WO | 2005080060 A1 | | 9/2005 | | |
| WO | WO-2008135757 A1 | * | 11/2008 | ........... | B30B 11/246 |
| WO | 2012157912 A2 | | 11/2012 | | |

OTHER PUBLICATIONS

Machine Translation of WO 9521633 A1 (Year: 1995).*
NPL-1.PCB Heater (Diy Joule heating). Sep. 9, 2012. Instructables.
Machine Translation of JP 2007001153 A.

* cited by examiner

APPARATUS AND METHOD FOR VOLUMETRIC REDUCTION OF POLYMERIC MATERIAL

CROSS-REFERENCE TO RELATED APPLICATIONS

This application is a Continuation application of U.S. Ser. No. 14/230,763 filed on Mar. 31, 2014, which claims priority of patent application no. GB1306653.5, filed Apr. 12, 2013. The entire content of each application is incorporated herein by reference.

BACKGROUND

Disposable synthetic polymeric textile materials are used particularly in hospital operating rooms as a sterile cover to protect patients and instruments from contamination and cross infection. Generically the material is known as sterile wrap or "Blue Wrap" and is available in many proprietary brands such as "Kimguard™" manufactured by the Kimberly Clark Corporation, and "DuraBlue™" manufactured by Cardinal Health. Other synthetic materials are known and used in hospitals such as Tyvek™ manufactured by Dupont.

The material is generally manufactured from non-woven synthetic polymers such as polypropylene or polyethylene and has the advantage of being tough and difficult to tear, non-absorbent, easy to manufacture in different sizes and is supplied as a sterile product. The material can also be manufactured to allow a predetermined air flow through the material when it is desirable to do so. Typically the material is manufactured from 100% polypropylene with a SMS (spunbond-meltblown-spunbond) structure. The material can be manufactured to allow a predetermined airflow through the material when it is desirable to do so. Other disposable products that are manufactured from these and similar materials include irrigation bags, hypodermic syringes, specimen and instrument trays, disposable forceps and sharps devices and medicine delivery systems, all can be processed by the current invention.

The disposable material offers many financial advantages over traditional textiles which necessitate high energy costs to launder them together with the use of potable water and chemicals such as detergents which can pollute downstream water courses. After use the material is categorised as either inert waste or bio hazardous waste and is usually disposed of by either incineration or landfill. It is estimated that globally 7000 tonnes of such material is destroyed daily after a single use. This material is potentially a valuable resource for recycling but issues in respect of sanitation and high volume to weight ratios make transportation expensive.

It is known that mechanical compaction machines or balers have been used to try and reduce the volume of the material for transportation but these are not efficient as the material exhibits "memory" and re-expand after compression, are slow and labour intensive to operate and the material still requires handling as bio hazardous material.

Reference is made to EP0556282 by the present inventor. These machines (inventions) were developed to volumetrically reduce foamed plastic products such as expanded polystyrene or styrofoam fish boxes. The machines comprise of electrically heated vessels and the material is melted and converted to a liquid which flows into a receptacle below the heated plates.

As the "blue wrap" synthetic textile material exhibits totally different melting characteristics to expanded polystyrene then such an apparatus is not suitable for volumetric reduction and sterilisation. This is because the density of the expanded polystyrene is significantly less than the synthetic textile material as it is cellular with large voids between the thin cell walls. As a consequence, on application of relatively low heat, the thin cell walls of the expanded polystyrene rupture and lose their physical integrity and will flow down a relatively shallow draft angle of the heated plates within an incline range of 45 to 60 degrees to a vertical axis which is advantageous as it allows a larger surface area inside a small machine to deal with a product that has a very unfavourable and high volume to weight ratio.

The synthetic textile material would not melt in a similar manner for several reasons. This is a result of molecular orientation and the manner in which polymer chains position themselves in the melting cavity. Polymers near the wall of the heated plates orient themselves by straightening out, while polymers near the centre of the load placed in the machine tend to stay coiled and do not melt. As a consequence confirmation when testing resulted in the un-melted material remaining static and inhibiting the melted material from flowing as was anticipated.

The primary reason is considered to be the textile material, compared to expanded polystyrene is denser and has thicker cell walls as a consequence a different polymer chain. From experiment it was found that the thicker cellular walls of the material acted as an insulator and would not allow heat to be conducted easily into the subsequent multiple layers of material that were placed in the machine for melting. As the material is a textile with a large surface area, increases in temperature also did not assist as they created a thermal uplift which moved the heated material away from the conducted heat source so a partial melt only was achieved which did not flow. It was also apparent that the temperature at which the material plasticises was considerably higher than expanded polystyrene.

FIELD OF THE INVENTION

The present invention provides a method and apparatus to both volumetrically reduce polymeric textile material and also polypropylene at the point of its use and to sterilise it.

SUMMARY OF THE INVENTION

The objective of volumetric reduction and sterilisation of the material is to allow the material to be transported without expensive specialist waste handling techniques to a recycling facility. At best the material will be recycled into other useful products and at worst it will be significantly volumetrically reduced or densified to considerably reduce the energy cost and environmental impact of transporting the material for any other method of disposal.

According to the present invention there is a thermal compacting apparatus for thermally compacting a polymer comprising a first and second heated surface inclined downwardly towards each other and provided with a passage at their lower ends through which melted polymer may drain.

The apparatus is beneficially a polymeric textile and/or polypropylene thermal compacting apparatus, and even more beneficially a synthetic non-woven polymeric textile and/or polypropylene thermal compacting apparatus. "Blue wrap" is such a material.

Such an apparatus is beneficial as waste synthetic polymeric textile material and polypropylene can be thermally compacted at source and will include materials, for example, to include sterilised sheets in various sizes, clothing and uniforms, bedside and window curtains, cleaning cloths, instrument pouches and any other product manufactured of synthetic polymeric textile material, and other products such as polypropylene saline bags. This provides a significant benefit of providing a volumetrically reduced and sterilised product that can be recycled and also significantly reduces transportation costs associated with a high volume product. The apparatus is also suitable for thermally compacting and sterilising other polypropylene products such as saline bags.

The first heated surface is beneficially inclined at less than 45 degrees to a vertical axis, and preferably the second heated surface is inclined at less than 45 degrees to a vertical axis. It has been determined that such a range of incline is beneficial as it was unexpectedly found that although the synthetic polymer textile material was able to melt and collapse by using a prior art arrangement such as described in EP0556282, it did not flow because the material simply collapsed and remained on the heated surfaces and eventually carbonised. Increasing the incline of the first and preferably second heated surface resulted in improved flow of the melted product.

The first heated surface is beneficially inclined to a vertical axis of between 25 degrees and less than 45 degrees, and preferably wherein the second heated surface is inclined to the vertical axis between 25 degrees and less than 45 degrees.

The first heated surface may be inclined at an angle of between 25 and 45 degrees to a vertical axis and preferably wherein the second heated surface is inclined at an angle of between 25 and 45 degrees to a vertical axis.

The first and preferably the second heated surfaces are beneficially arranged to be heated to a temperature in the range 250° C. to 310° C., and more preferably between 275° C. and 295° C. and even more preferably at substantially 285° C. The first and preferably second heated surfaces include at least one heating element. Utilising the claimed temperature ranges also ensures sterilisation of the material. The arrangement of EP0556282 is incapable of operating at such temperatures. During the process of converting the material from a solid to a liquid the temperatures utilised have been found to destroy biological pathogens. This is assisted by the fact that during the process the material flows into a receiver as defined below that keeps the material at a raised temperature such as 260° C. for 30 minutes. This is important because "dry heat" is not always successful in sterilisation and the presently claimed apparatus and process can be considered to provide "conductive wet" heat.

Unlike conventional plastic injection moulding, vacuum forming or extrusion processes which are commonly used to melt and mould polypropylene materials, the process temperature of the invention is different and has been determined to fall within the claimed temperature range. This is because the other conventional methods of melting and forming the material utilise not only heat but pressure such as a mechanical screw or a vacuum to assist in processing. Unlike this equipment the invention does not require pressure but relies on gravity to feed the machine so the melting temperature is crucial as too low a temperature inhibits the process and too high a temperature can damage the melt index of the material making it unsuitable for recycling or in severe instances it could create a combustion risk. The temperature range is beneficially controlled by maintaining power to the heater plates on demand via contactors or solid state relays which switch on power as a result of a programmable logic controller or temperature controller sensing the set operating temperature via, for example, thermocouple sensors which are positioned inside the body of the material that provides the heated surface(s). The heated surfaces are each beneficially provided by aluminium plate heaters having at least one heating element therein. The heating element may be an electric resistance heater for example. An improved plate heater is achieved through provision of a sprayed (preferably plasma) heating element which in itself is in plate form. A preferable structure is a substrate which can be made of stainless steel, fibreglass or silicon for example. A plasma sprayed heater layer is provided thereon, preferably separated from the substrate by an insulator material, and a final insulation layer is provided onto the heating layer. This achieves a very thin heater plate and thus achieves fast heating and cooling.

The temperature profile of the first and preferably the second heated surfaces may increase towards the passage. The at least one heating element in the first and preferably the second heated surfaces is beneficially configured such that the temperature profile of the first and preferably second heated surfaces increases towards their lower ends and the passage. This further improves in melting and transfer of the material towards the passage. The temperature range of the first and beneficially second heated surface changes between substantially 260° C. at a leading edge to substantially 295° C. at an edge adjacent the channel. This assists in achieving a tumbling effect on the material. This creates a physical phenomena whereby the faster melting material plasticises and 'slips' or moves downwards in a fluid manner to exit the heating zone and creates a void which encourages the material above it to fill. This is contrary to common practise in waste material processing where heating plates are designed to ensure predictable and even heat transfer.

The first and second heated surfaces beneficially define a heating zone therebetween.

A further problem is that on leaving the heated zone and flowing through the passage the material has a propensity to solidify and as a consequence create solidified pillars of material between the heated surfaces and the receiver which creates a blockage and stops the removal of the receiver from the machine. Furthermore, at the end of a melting cycle when the heated surfaces are cooling and the heating elements isolated from power, residual amounts of material are left on the heated surfaces as the heated surfaces, which may be aluminium plates or printed circuit board plates, cool quickly.

A lower end(s) of the first and preferably second heated surfaces beneficially includes an insulating material for reducing the rate of cooling of the first and preferably second heated surfaces. The insulating material is beneficially provided applied to the heated plate and is beneficially provided on the heated plate out of or away from the flowpath of the material. This encourages material to vacate the plates and to exploit residual latent heat. A layer of micro-porous insulation is beneficially utilised. It is preferably applied to the rear of the two main plate heaters to assist the final moments of the process.

The passage beneficially comprises a longitudinal length and a width, where the width is preferably in the range 15 mm to 75 mm. The longitudinal length is parallel to the leading edge of the first and second plates. It is important that the separation between leading edges of the plates, analogous to the width of the passage, is carefully selected. A range of 15 mm to 75 mm is a workable range, however, a reduced separation is preferred for pure forms of waste material whereas a passage width of 75 mm can accept a significant variety of mixed waste. For example, as well as polymeric textile material and/or polypropylene other materials in the waste may be present such as Velcro, nylon cuffs, metal poppers etc which may not melt. However, it is beneficial that these materials are encapsulated in the melted and subsequently solidified waste material. For this reason a greater width of the passage is beneficial to ensure that this material may pass therethrough. As such it has been found that substantially 70 mm of separation between the plates is optimal for mixed waste material.

A receiver is beneficially disposed in a receiving zone for receipt of melted synthetic textile material from the passage. A heating element is beneficially provided configured to supply heat to the receiver. The receiver is beneficially heated in order that the material flows onto a heated surface and does not immediately solidify. This ensures flow of the material, and also provides a dwell time for the material to ensure sterilisation. The dwell time may for example be between 15-60 minutes with a preferred dwell time being substantially 30 minutes. The temperature may be at approximately 260° C. The heating element beneficially comprises a heating plate. The receiver is beneficially removably mounted with respect to the heating plate.

A cooling arrangement is beneficially provided for cooling the receiver. The heating element and cooling arrangement beneficially provide a changeable heating and cooling surface for heating or cooling the receiver as appropriate. The heating and cooling element may therefore preferably be integrated to provide an optional heating or cooling surface for heating or cooling the receiver. The receiver beneficially takes the form of a tray. Even more beneficially, the receiver is in the form of a mould receptacle.

The apparatus beneficially comprises a housing for accommodating the first and second heated surfaces wherein the housing is in fluid communication with a filter arrangement for filtering gases received from the housing, the apparatus further comprising a condenser arrangement positioned intermediate the housing and the filter arrangement. The filter arrangement is arranged to receive output gases from the housing. Such gases may be harmful and it is important that these are filtered prior to release to the atmosphere. It is beneficial to provide a condenser arrangement positioned intermediate the housing and the filter arrangement in fluid communication with both the housing and filter arrangements. The condenser arrangement provides a significant benefit in that it reduces the temperature of the exhaust gases from the housing and condenses any fluid which is in the exhaust gases. This improves the effectiveness of the filter arrangement and minimises the impact of the apparatus with respect to release of odours.

The cooling arrangement beneficially includes a heat exchange unit (commonly termed a chiller unit in this field) and heat transfer arrangement in fluid communication, wherein heat from the receiver and/or the heating element if transferred to the heat transfer arrangement. An expansion tank is beneficially positioned intermediate the heat exchange unit and the heat transfer arrangement and in fluid communication with both the heat transfer arrangement and the heat exchange unit. As the melted waste material has to be reduced in temperature to make it safe to handle this is achieved utilising a cooling arrangement made up of a heat exchange unit and heat transfer arrangement. To improve the efficiency of the heat exchange unit and to prevent damage, an expansion tank is beneficial intermediate the heat exchange unit and heat transfer arrangement to act as an additional heat sink to assist in reducing the process temperature.

After a predetermined period of time and temperature the heating elements in the machine are isolated and cool down to allow the solidification of the material and its removal from the machine. In certain applications such as large teaching hospitals with several operating rooms, the throughput of the machine would be insufficient to cope with demand as a result of the time it takes to cool the liquefied material. Accordingly, a heated plate may be provided under the receiver which would also contain cooling circuits which would be operated at the end of the heating cycle to accelerate the cooling time of the machine.

A cooling zone may be provided remote from the receiving zone and heating element (if provided) and a transfer arrangement is beneficially provided for transferring the receiver to the cooling zone. A plurality of individual locations within the cooling zone is beneficially provided each configured to receive a receiver. This means there can be cooling of more than one filled receiver simultaneously. This means that air cooling can be utilised. Such a transfer arrangement enables cooling of the waste material in a receiver without the essential requirement for a cooling arrangement. This is beneficial for certain applications as the cost of the equipment may be reduced due to the removal of the requirement for a cooling arrangement. An additional benefit is that high volumes of material can be processed as cooling of a receiver can be achieved at the same time as processing of further waste material into a further receiver. The transfer arrangement may be of a different form and may comprise, for example, movement of the receiver on a roller bearing track, high temperature conveyor or a carousel arrangement.

The first and preferably the second heated surfaces are preferably defined by first and preferably second heating plates respectively. The first and preferably second heating plates may be formed of aluminium which is preferably cast. The plates beneficially incorporate at least one heating element therein. The heating elements are beneficially electrically heated.

It is beneficial that the first and preferably second heated surfaces are provided by printed circuit board plates. Such plates are beneficial as they are significantly reduced in thickness compared to traditional aluminium heating plates meaning that the plates may be heated up to the desired temperature significantly quicker than with an aluminium cast plate.

The first and preferably the second heated surfaces are beneficially formed with a coating thereon to assist transfer of material thereover. A suitable coating is, for example, Teflon®.

A monitoring and recording arrangement is beneficially provided for monitoring and recording first and preferably second heated surface temperatures and preferably dwell time of melted material transferred through the passage to the receiver. This is beneficial to ensure that the material is sterile and has been processed at a sufficiently high temperature and dwell time to ensure complete sterility of the processed material.

An exhaust arrangement is beneficially provided for removing gases from the process.

A door lock is beneficially provided configured such that the door cannot be opened to the apparatus until the temperature within the apparatus has dropped to a safe level. Accordingly, the apparatus comprises a door which is beneficially electrically operated. A sensor within the apparatus is arranged to measure the temperature within the apparatus. It is beneficially provided with a control arrangement which controls the door lock. The controller arrangement beneficially includes a monitoring and recording arrangement.

Also according to the present invention there is a method of thermally compacting polymeric textile materials and/or polypropylene comprising the steps of introducing polymeric textile material and/or polypropylene into a heating zone defined between first and second heated surfaces inclined downwardly towards each other and being provided at their lower ends with a passage through which polymeric textile material and/or polypropylene may drain.

BRIEF DESCRIPTION OF THE DRAWINGS

The present invention will now be described by way of example only with reference to the accompanying drawings in which.

DETAILED DESCRIPTION OF THE INVENTION

Figure 1:
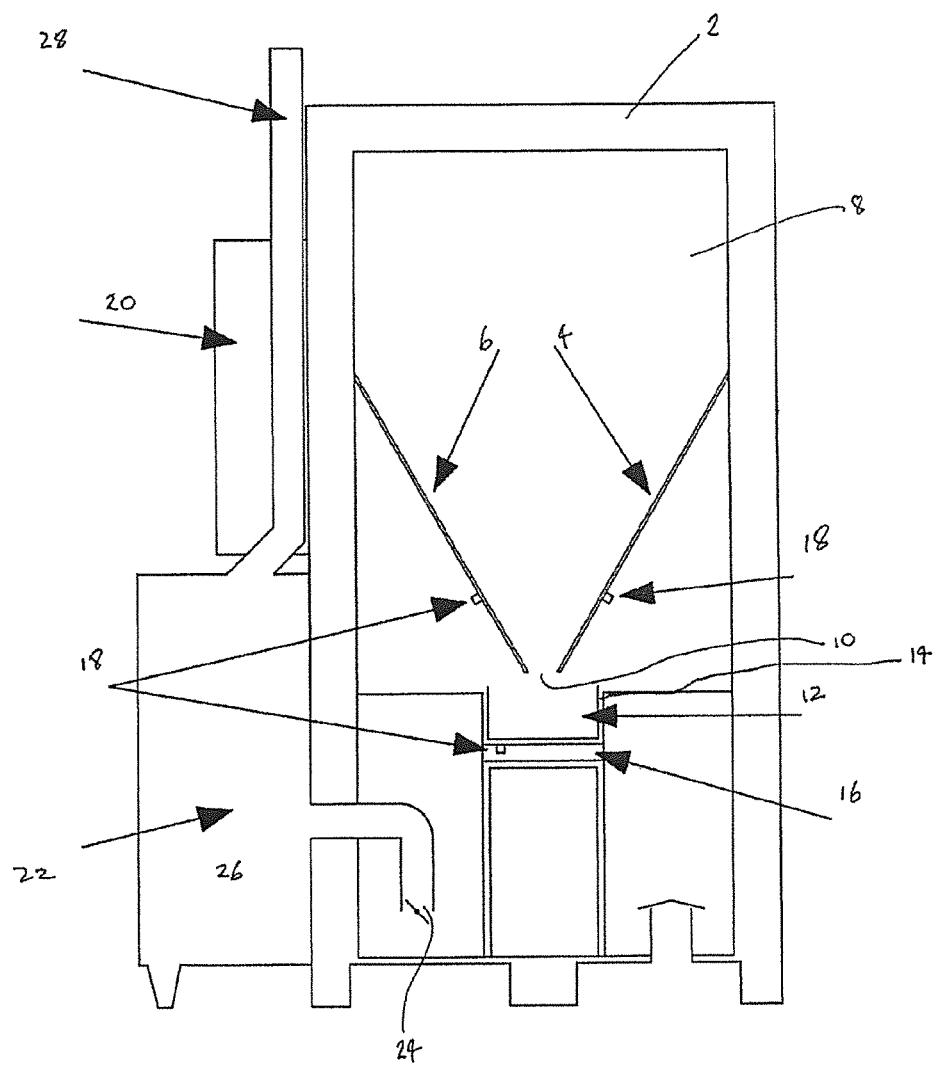
FIG. 1 is a schematic front view of an apparatus according to an exemplary embodiment of the present invention.

Referring to FIG. 1 there is an exemplary embodiment of the present invention. The apparatus is shown without a door which is closed during use and hides the internal components provided within the housing (2) and provides a seal for when the apparatus is in use. The apparatus includes first and second heated plates (4,6) which are beneficially formed from cast aluminium and are electrically heated being provided within the housing (2). The housing (2) defines an opening (8) in its front. The first and second plates (4,6) are inclined downwardly configured to funnel waste material such as synthetic polymeric textile material downwardly toward a channel (10) provided between the lower ends of the plates (4,6). The waste material is therefore input into the housing (8) through the front opening, however, it is envisaged that one or more openings may be provided in another portion of the housing (2) such as in the top or in the side of the housing but beneficially above the first and second plates (4,6).

In the examples shown the first and second plates have identical angles relative to the vertical axis. It will be appreciated, however, that the angle of the first and second plates may be different to each other. The incline angle of the heated surfaces to the vertical is beneficially less than 45 degrees, and is beneficially in the range 25 degrees to less than 45 degrees. This is to ensure that the material melts and collapses and subsequently flows through the channel (10).

The first and second plates (4,6) are beneficially coated with Teflon®, and may be ceramic or hard anodised. A receiver (12) is provided supported below the channel (10) arranged to collect melted material therefrom. The receiver (12) removably seats into a docking zone (14) which is provided to ensure alignment of the receiver (12) with the channel (10). The receiver (12) seats onto a plate (16). The plate is beneficially arranged to be heated and includes one or more heating elements therein, preferably of the type of electrically resistive heating elements. The plate (16) may also include one or more cooling circuits comprising a channel to transfer coolant therethrough for increasing speed of material processing. The plate (16) also includes a thermocouple to monitor the temperature of the plate (16). Thermocouples (18) are also provided on the heated plates (4,6) to monitor temperature. Temperature information from the thermocouples (18) is transferred to a control arrangement (20). The control arrangement (20) includes a control panel and serves to control the electrical supply to the heating elements within the heated plates (4,6) and the plate (16). The control arrangement controls the time of heating of the heated plates (4,6) and the plate (16) and also controls actuation of the cooling circuit in the plate (16). The control arrangement also provides control to an extraction arrangement (22) which includes a filtration cabinet for transfer of gases from the apparatus through an inlet (24), through a filtration cabinet (26) and out of an exhaust (28). Material leaving the heated zone defined between the heated plates (4,6) and flowing into the receiver (12) has a propensity to solidify and as a consequence creates solidified pillars of material between the heated plates (4,6) and the receiver (12) which can create a blockage and stop the removal of the receiver from the apparatus. Furthermore, at the end of a melting cycle when the electrical plates are isolated from power, residual amounts of material may be left on the plate heaters as the aluminium cools quickly. To encourage material to vacate the plates and to exploit residual latent heat it has been determined that a layer of micro-porous insulation should be applied to the rear of the two main plate heaters to assist the final moments of the process. It has also been determined that to assist in the material sliding down the plates it is preferable to coat them with a polytetrafluoroethylene (PTFE) or Teflon® coating. This assists the process by sealing the porous surface of the aluminium electrical heat plate heaters which enhanced the material's passage or slip factor as it did not permeate into the surface of the plate heaters when fluid. The PTFE's melting temperature is typically 326° C. but the operating temperature of the Teflon® during the heating process is less than 200° C. making it suitable for purpose in respect of health and safety issues.

It is further improved by the provision of the heated plate (16). It is preferred that the temperature of the heated plate (16) is set to be approximately 20° C. lower than the set point of the heated plates (4,6). From trial it has been determined that the optimum temperature of the plate (16) is 265° C.

After a predetermined period of time and temperature the heating elements in the machine are isolated and cool down to allow the solidification of the material and its removal from the machine. This is following a material dwell time within the receiver where heat is supplied ensuring sterilisation of the material.

It has been determined that in certain applications such as large teaching hospitals with several operating rooms, the throughput of the machine would be insufficient to cope with demand as a result of the time it takes to cool the liquefied material. In this situation it is intended that in one embodiment the heated plate under the removable receiver (12)

would also contain cooling circuits which would be operated at the end of the heating cycle to accelerate the cooling time of the machine.

Figure 2A:
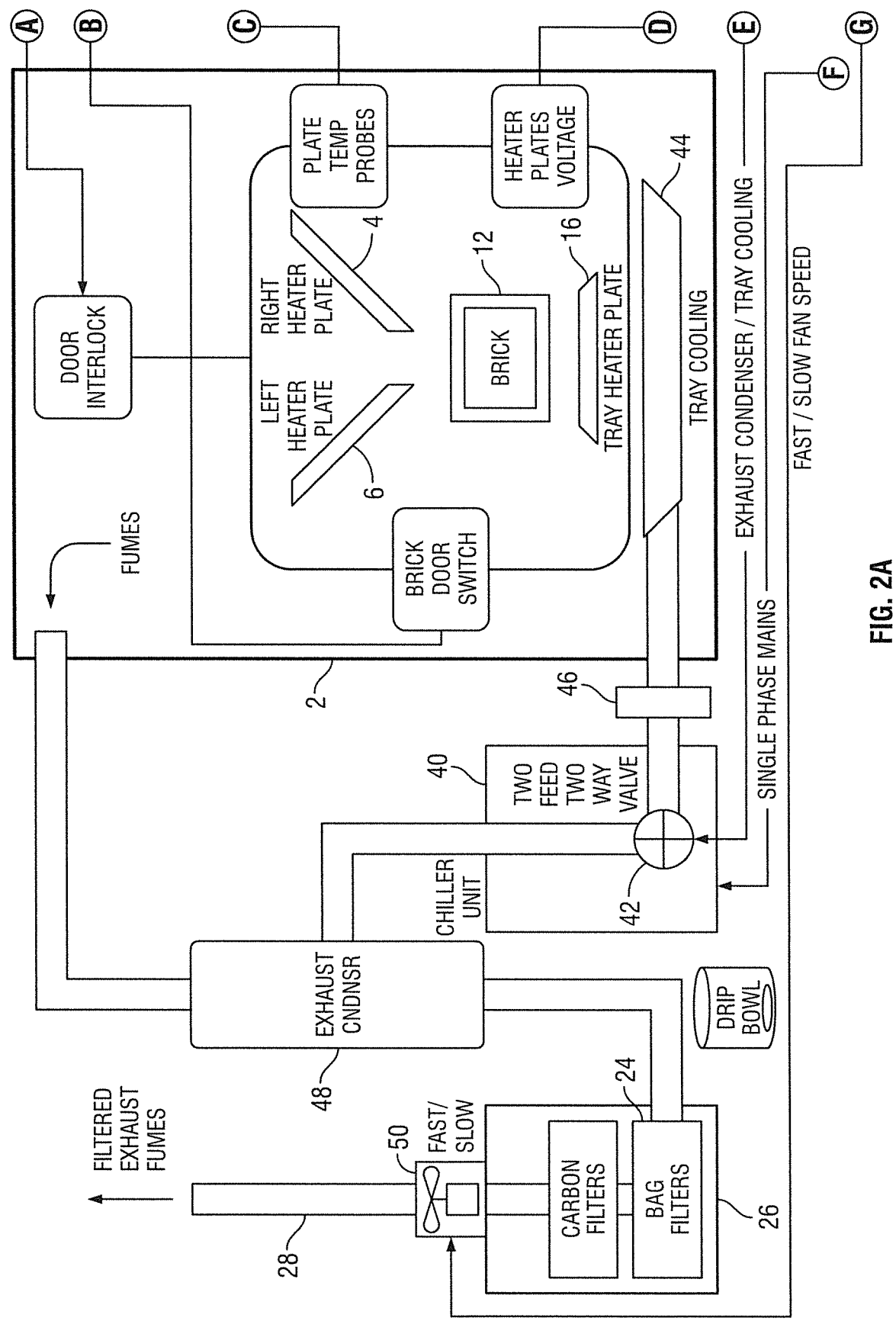
FIG. 2A is a more detailed schematic representation of an apparatus according to an exemplary embodiment of the present invention showing an optional cooling arrangement.
Figure 2B:
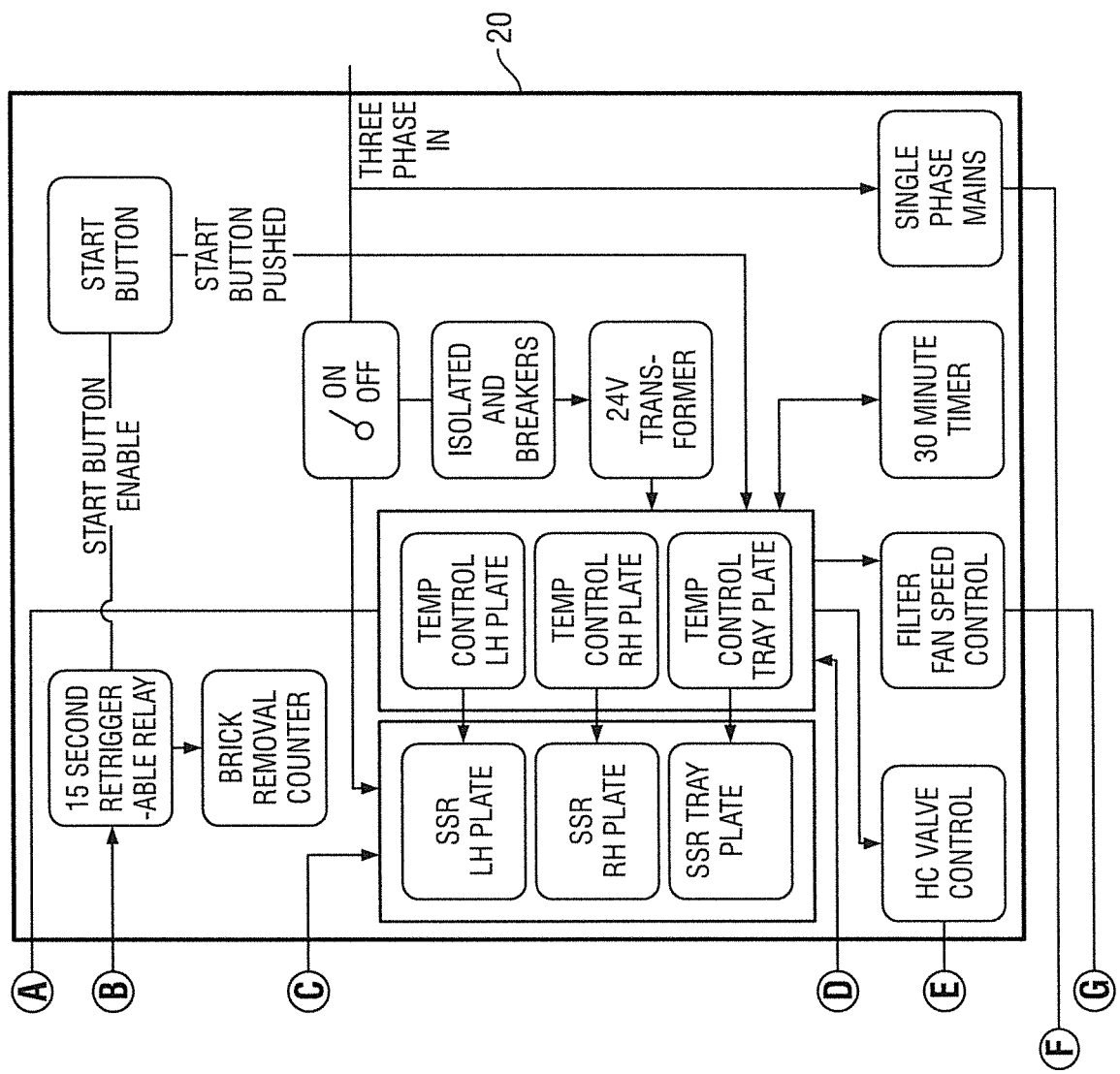
FIG. 2B shows an exemplary control panel.

The receiver (12) may rest or be otherwise disposed on the heated plate (16) wherein the heated plate (16) may be cast aluminium. In the event that the heated plate also comprises cooling elements, circuitry fluid is passed through the cooling pipes which may have been chilled with an industrial chiller to sub-zero temperatures. This fluid has an inhibitor added such as glycol to stop it from freezing. At the end of the heating cycle the fluid can be diverted, for example, from the heat exchange unit (40) as represented in FIG. 2 via a two-way solenoid valve (43) where the fluid is violently converted to steam. The calorific conversion from fluid to steam acts to initiate an immediate and rapid drop in temperature. The cooling fluid can be supplied with or without the addition of chemicals to inhibit the freezing temperature of the fluid and can be delivered in addition to the heat exchanger (chiller machine) by simply attaching to a mains water supply with our without pumps and a water tank as either an open or closed circuit. It will be further appreciated that the cooling arrangement may comprise a heat transfer arrangement which is alternative to the cooling circuit provided within the heating plates. Such a heat transfer arrangement or cooling circuit may be provided separate to the heated plate (16) as represented by reference number (44) in FIG. 2. A heat transfer arrangement (44) independent of the heated plate (16) or a heat transfer arrangement comprising cooling circuits within the heated plate (16) are envisaged. It is further envisaged that intermediate the flowpath between the heat exchange unit (40) and the heat transfer arrangement (44) is an expansion tank (46). At the end of the heating cycle the melted waste material has to be reduced in temperature to make it safe to handle. As described this is typically via a heat transfer arrangement comprising a cooling circuit provided within the heated plate (16). At the end of the heating cycle the two-way solenoid valve (42) shares flow of cooling fluid from a condenser arrangement (48) which is positioned intermediate the flowpath between the housing (2) and the filter arrangement (26). As the heated plate (16) is operating in excess of 200° C., the initial flow of fluid converts to superheated steam and this calorific conversion is fundamental to the cooling process as this accelerates the cooling of the heated plate (16). At this temperature and pressure the return flow would ordinarily damage a conventional heat exchange unit accommodated in a chiller machine so an expansion buffer tank (46) is connected in fluid communication between the heated plates (16) and the heat exchange unit (40) to avoid damage and to act as an additional heat sink as the surplus fluid in the expansion buffer tank (46) assists greatly in reducing the process temperature.

It has also been determined that the assisted cooling of the material after melting offers a considerable reduction in odour. The melted material does not liberate VOC's as the process can be considered a simple reversal of the original manufacturing process but as the polymer under temperature is an aromatic it is desirable to remove odours which could be unfamiliar in the workplace operating the machine. As the melting polymer is an aromatic an embodiment of the invention will utilise a variable speed exhaust fan (50) which will accelerate at the end of the process when the access door (not shown) is opened to reduce the emissions of odour. This fan (50) also assists in cooling the machine at the end of the heating process and to maintain a partial vacuum in the machine to reduce the opportunity for odour to escape from the machine. The exhaust (28) from the machine is filtered through a filter arrangement (26) preferably comprising both a HEPA and activated carbon filter to reduce emissions in respect of fumes and odour.

During operation of the apparatus a partial vacuum is maintained in the housing (2) (cabinet/hopper) while maintaining a flow of air from the housing using the electric fan (50) which flow is conveyed into the filter arrangement (26). The fan is beneficially a variable speed fan and works at low speed when the waste material is being heated and at high speed during the cooling cycle or when the door of the housing (2) is open. The purpose of the partial vacuum is to eliminate emissions of unfamiliar odours into the workplace from the housing (2) and the purpose of the filter arrangement (26) is to reduce the odour of the exhaust gases to the atmosphere.

Figure 5:
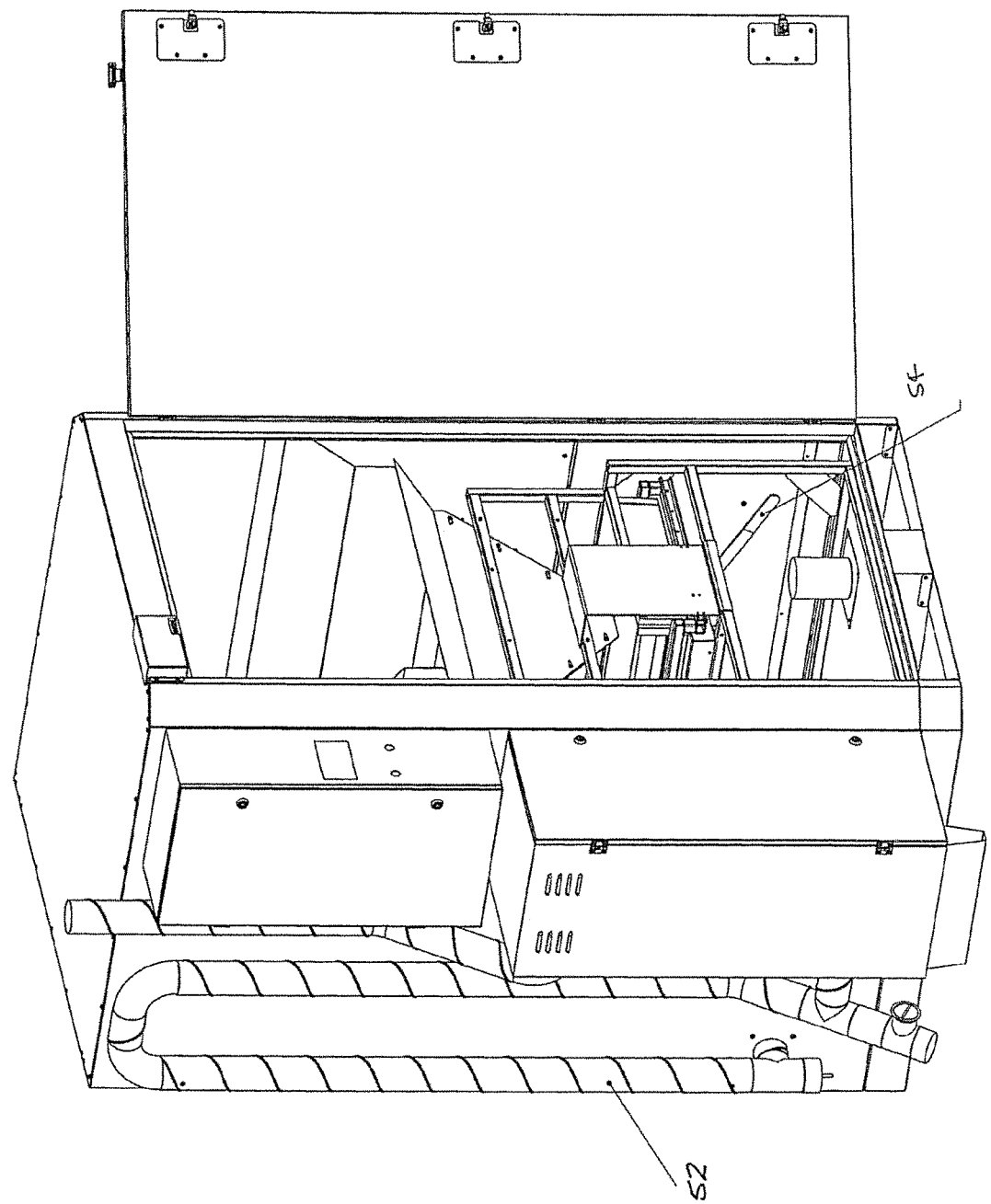
FIG. 5 is a schematic perspective view of an exemplary embodiment of the present invention showing in addition a cross sectional view through an example of a component of the condenser arrangement.
Figure 5:
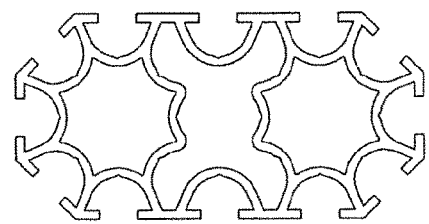

The exhaust fumes are hot and can contain plasticising oils that are liberated from the polymer during the process. The fumes are passed through the filter arrangement such as a paper or textile bag filter and then through an activated chemical filter such as a carbon filter to minimise odours from the machine. Filters can lose their efficiency if hot fumes are passed through them and their longevity is reduced if they become blocked with plasticising oil. To reduce the temperature of the exhaust gases before they reach the filter arrangement (26) and to capture any plasticising oils, the gases are passed through a condenser arrangement (48). This may comprise a condenser plate which may consist of a hollow aluminium finned vessel. The condenser plate may, however, be made of any conductive alloy. The vessel is finned to increase the surface area in contact with the airflow. During the operation of the apparatus, a chilled fluid is passed through this vessel which assists in reducing the temperature of the exhaust gases and also assists in condensing any fluid which is in the exhaust gases. The fins of the condenser are represented in FIG. 5 and are beneficially vertically aligned allowing the collected fluid to flow easily downwards to a point at which they can be collected for disposal or recycling. It is also possible to utilise, in an alternative configuration, a spiral helical finned tube to achieve the same effect. The exhaust pipe (52) as best shown in FIG. 5 is elongated to increase the dwell time of the exhaust gases.

To ensure the safety of operators an electrical door lock may be utilised which will not allow the door to be opened during the process until the temperature of the inside of the machine has dropped to a safe level. This electrical door lock will be interlocked with the temperature control software running in the control arrangement (20) and the machine and will only open when thermocouple sensors confirm the ambient temperature inside the machine.

It is anticipated that the machine will be fitted with a telemetry devices to allow the machine operators from a distance to interrogate and log the machine cycle times and record any deviation from normal operation which may necessitate investigation or repair.

The apparatus may be manufactured from stainless steel material as it is intended to be used out of doors but alternatively could be manufactured from ordinary steel with a protective coating or even an insulated polymer such as GRP.

As the apparatus ensures sterility of the material after melting an embodiment of the invention contains a data logger to record both time and temperature to confirm that the material has been processed at a sufficiently high temperature and dwell time to ensure complete sterility of the processed material.

Figure 3:
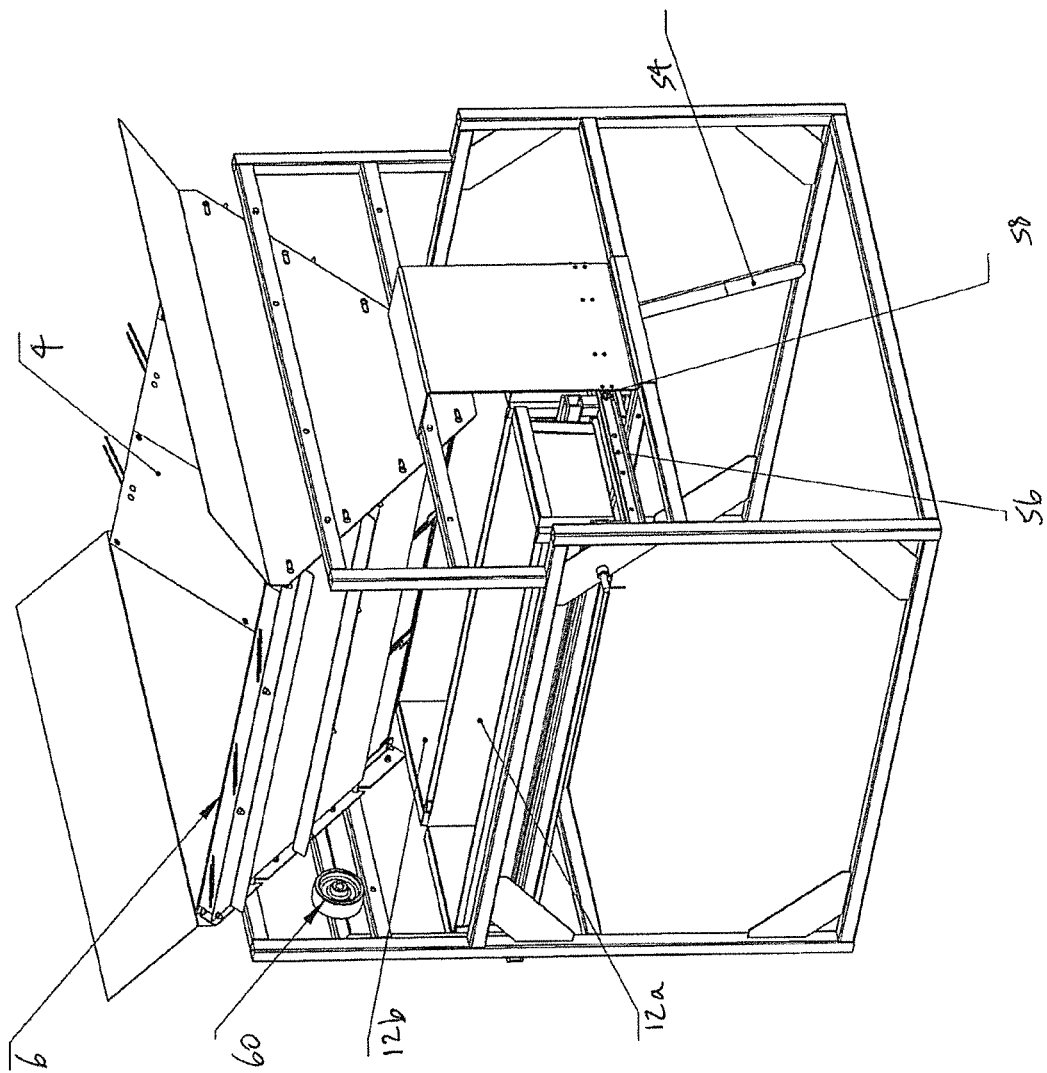
FIG. 3 is a schematic perspective view of an exemplary embodiment of the present invention with the housing removed.

Referring now to FIG. 3, there is a schematic perspective view of an embodiment of the present invention that utilises a different cooling mechanism to the arrangement as presented in FIG. 2.

The apparatus as previously described utilises fluid and air cooling to make the processed material safe to handle by solidifying the liquid polymer after the heating process. Whilst the process works and is satisfactory it is expensive as it requires a chiller machine, cast cooler unit, expansion tank and special solenoid valves and high temperature high pressure cooling.

In applications where high volumes of material are to be processed the cost/value benefit of the machine using this equipment works but in applications where there are lower volumes of materials the cost of this equipment may be prohibitive in the cost benefit relationship.

In such applications it is proposed to air cool the material and this is achieved by locating the receiver (12) on a transfer arrangement such as a roller bearing track, a high temperature conveyor or a carousel arrangement.

In this embodiment no cooler arrangement is used and typically the heating element is raised or lowered by a lever (54) to make contact with the receiver (12). At the start position the heating element (16) touches the receiver (12) during heating. At the end of the process the heating element (16) is dropped from the contact position by the lever and the full receiver (12) is moved sideways on the roller track to the cooling position and then cooled. An empty receiver (12) is then put into position and filled and at the end of the next cycle the receiver (12) is moved to the alternative cooled position. At the end of the third cycle the first cooled receiver (12) is either removed from the apparatus and stored in a rack or put into a storage position at the bottom of the apparatus until each position is full and the first block is then removed. In this instance the material has the benefit of several hours of cooling without the need for forced fluid cooling by a machine.

Figure 4:
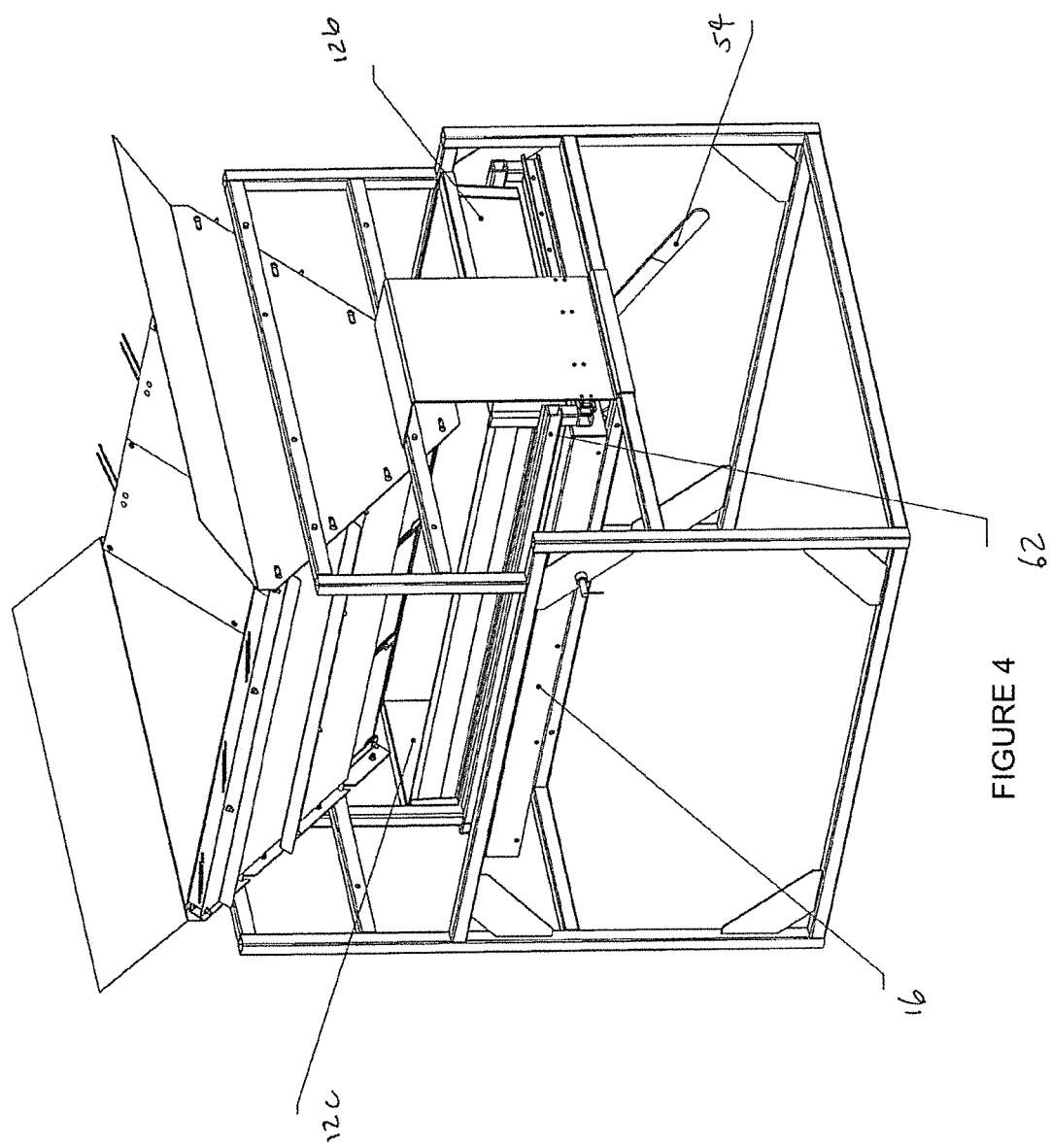
FIG. 4 is a schematic perspective view of an exemplary embodiment of the present invention as shown in FIG. 3 in an alternative operational configuration.

As such as presented in FIG. 3, receiver (12a) is in the cooling configuration and receiver (12b) is in the receiving configuration. Further shown is rail (56) along which the receivers can slide along sliders (58). The handle is presented in the raised or 'on' configuration which means that the receiver receiving the waste material is prevented from moving. Rear carriage supports (60) are identified. FIG. 4 presents the same embodiment as presented in FIG. 3, however, the fill receiver (12b) has moved to a cooling position and a new empty receiver (12c) has been moved across to receive waste material. The heating element (16) can be seen and the handle (54) is shown in the lowered or 'off' configuration allowing the receiver carriage (62) to move.

In one embodiment forced air cooling can be achieved utilising vortex blowers. In this device compressed air is blown through a vortex blower which cools the air to a very low temperature (sub-zero) and as a consequence the material cooling is accelerated but without the need for a chiller machine.

Figures 6A, 6B:
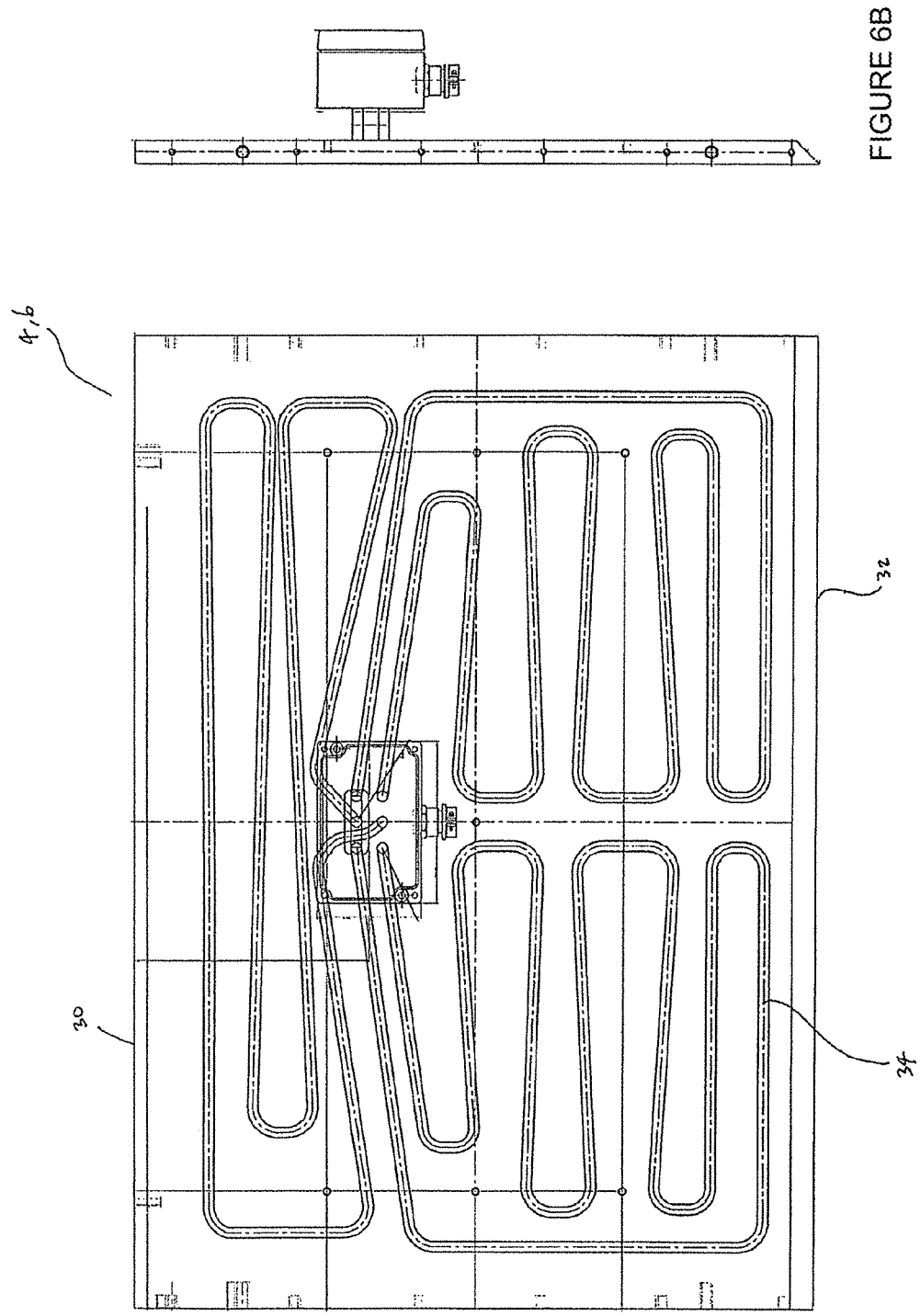
FIG. 6a is a schematic cross-sectional plan view of a heated plate according to an exemplary embodiment of the present invention.
FIG. 6b is a schematic cross-sectional view of an end of the heated plate.

Referring to FIG. 6 there is a schematic plan cross-sectional view through an exemplary embodiment of a heated plate (4,6). The heated plate (4,6) comprises a first or upper end (30) and a lower or second end (32), where the second or lower end form one edge of the channel and the other of the first or second heated plate 4,6 forms the other edge of the channel. The lower edge (32) is beneficially chamfered as shown in FIG. 6b. It will be appreciated from FIG. 6a that the heating effect of the heating element (34) is greater towards the lower edge (32) as a result of increased volume of heating element toward the lower edge (32). This is provided to ensure continuous process of melt and flow of the waste material.

It was discovered from trial that although the largest manufacturer of the sterilisation wrap's melting point was cited at 150° C., the heating source acted as a heat sink and consequently at this temperature the material did not flow. To achieve a temperature conducive to achieving a continual process of melting and flowing and to account for thermal lag the heat source which is preferably electrical resistance heaters have to operate to provide a heated surface temperature of between 275° C. and 295° C. The optimum set point of these heated surfaces (plates) was determined to be 285° C. At this temperature the material will melt continually and the flow temperature rate is confined between 155° C. and 160° C. with the optimum temperature to achieve good flow rates being 156° C. At this temperature the melt index of the material is not degraded making the material suitable for recycling into new product or products.

Consequently the temperature range found to be suitable for the process is between 155° C. and 160° C. and this is controlled by maintaining power to the heated plates on demand via contactors or solid state relays which switch on power as a result of a programmable logic controller or temperature controller sensing the set operating temperature via thermocouple sensors which ideally are positioned inside the aluminium plate heaters near the area in which the process takes place.

The first and second plates consist of two cast aluminium electrically heated plate heaters which are Teflon® coated as described above to assist the passage of the material after melting and one mica insulated or cast aluminium plate heater (16) placed under the mould receptacle. It is anticipated that these heaters could also be simplified by welding or mechanically attaching round or square tubular mineral insulated electrical resistance elements to substantial aluminium, non-ferrous or ferrous plates which would reduce weight of the machine and the cost of casting and machining plate heaters. Non-ferrous materials are preferable to ferrous materials in the construction of the heating plates as they exhibit better thermal conductivity characteristics.

In an alternative embodiment it is beneficial to use a plasma sprayed heated plate to melt the waste material. The significant benefit of such heated plates is their lower mass which will allow much faster heating and cooling process times. Such heaters may be termed 'thermal spray heaters', and are constructed of layered structure comprising a substrate, and insulating layer, a heating plate plasma sprayed onto the insulating layer and a further insulating layer forming the outer heating surface of the heater plate.

Figure 7:
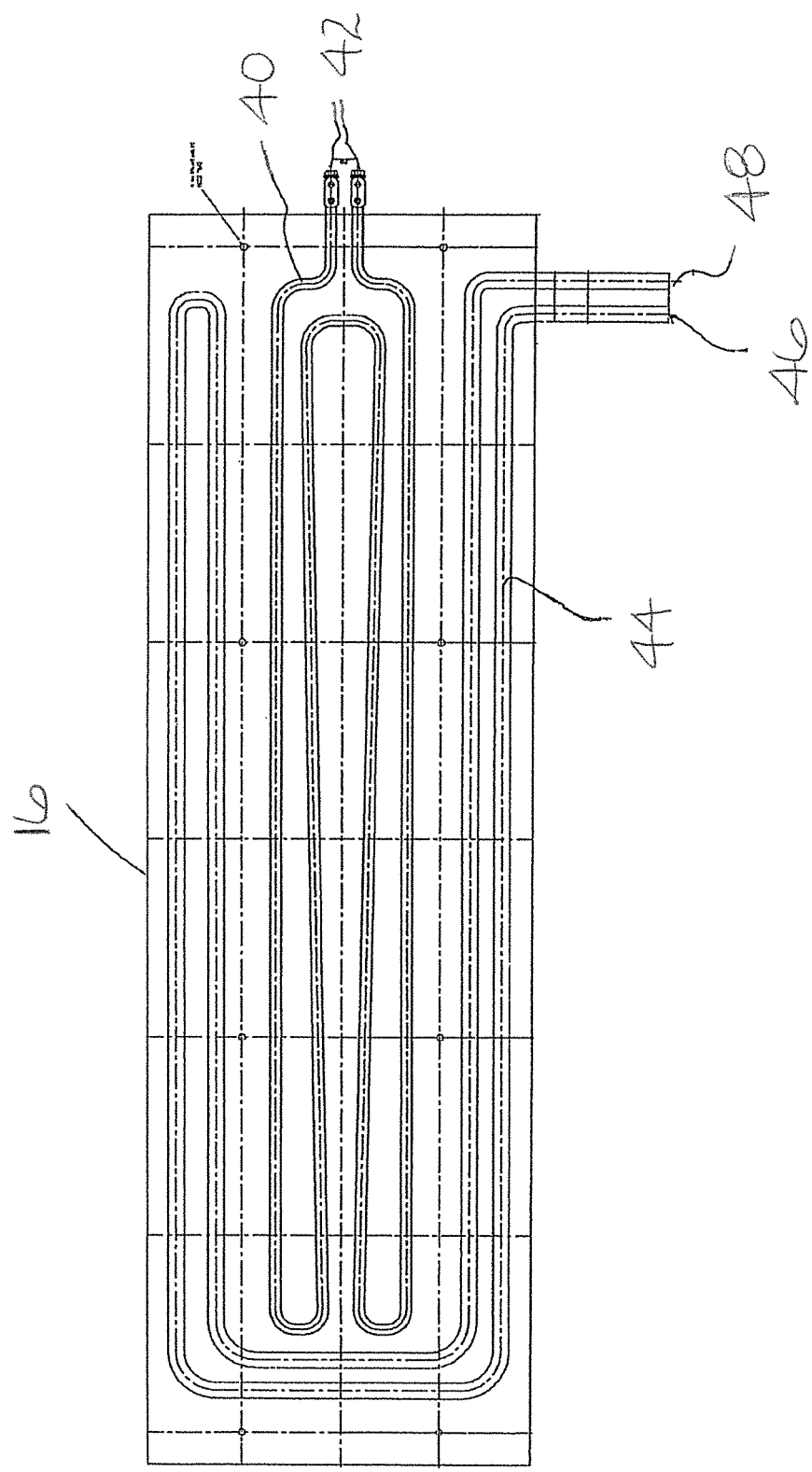
FIG. 7 is a schematic cross-sectional plan view of a heating and cooling plate for the receiver for use in an exemplary embodiment of the present invention.

The plate (16) is identified in FIG. 7 and is a schematic cross-section through a plan view of a traditional plate (16). An electrically heating element (40) is provided having electric terminals (42). Furthermore, a cooling circuit (44) is provided having an inlet (46) and outlet (48) to be used to increase productivity of the apparatus.

The walls of the housing are hollow and filled with body soluble insulation for the purpose of energy efficiency, process control and safety. The insulation can be made from fibreglass, ceramic, silica or other insulation.

To avoid heat transfer from the chassis of the machine cooling trays can be insulated with Aerogel material which is made from micro porous glass, silica or zeolite which protects the cooling tray from both radiant and conducted heat.

During research a problem was encountered with heat loss and excess temperature loss at the corners of the door of the machine which was sealed around the door with a high temperature seal that followed the 90 degree angle of the door shape. As a result of experimentation the door seal was changed to a shallow curve which created an air gap and stopped the heat losses.

There are a number of additional beneficial features of the present invention. The machine can be loaded continuously with a chute. The machine uses an increased airflow and a moving mould plate to eject blocks on a continuous basis. When the loading chute is opened the exhaust fan accelerates to stop fumes exiting the machine. In order to prevent degradation of the heated surfaces, an additional coating or anodizing is beneficial. This protects the heated surface and any coating thereon such as Teflon®.

The machine can be configured such that at the end of the day's operation or periodically can be switched into "clean" mode at which time the temperature in the machine increases to 400° C. to sterilize the internal surfaces of the machine.

The machine that has variable adjustments to allow it to melt all common polymers in addition to "Blue Wrap". The machine can be set to operate between 0-450° C. An atomiser nozzle may be positioned in the roof that can spray the inside of the machine with disinfecting fluids or chemicals as and when required either manually or automatically as part of a cleaning regime.

The machine is usually manufactured from stainless steel but can be manufactured from other metals or polymeric materials such as reinforced fibreglass and this may be painted yellow or white which is a colour known to repel flies.

Telemetry provides for cycle times and servicing can be interrogated at a distance and adjustments made to the machine. The machine can be scaled, so for example can be reduced in size for the melting of specific products for example masks or hats. The machine is fully insulated machine that can be used in any climate. The machine may also be fitted with a voice card which thanks the operator for loading the machine when the door or chute is opened and can advise on machine status or issue operating instructions.

The machine that is painted a particular colour to deter insects, and can be operated by induction heating not resistant heating and can be operated by heating with superheated fluids. The machine can be operated by heating with microwave emission.

Alpha numeric embossing may be provided in each receiver so each batch of material can be identified to a particular machine or location. A time and temperature data logger may be provided so each batch of material can be audited and an integrated alarm and notification produced if a batch does not achieve the pre-set process requirements.

In one exemplary embodiment the machine cleans emissions with a plasma burner to eliminate the requirement for a filtration system. A built in fire suppressant system may be provided to legislate for malicious damage or catastrophic failure of the control system. This is supplemented by a thermal fuse.

The present invention has been described by way of example only and it will be appreciated by the skilled addressee that modifications and variations may be made without departing from the scope of protection afforded by the appended claims.

The invention claimed is:

1. A method for volumetric reduction and sterilization of non-woven polymer textile, comprising the steps of:
   providing a polymeric textile product thermal compacting apparatus, comprising:
   a heating zone operable to melt polymeric textile product, the heating zone defined by and consisting of:
      opposing first and second heated sloped plates having respective opposing first and second heated sloped surfaces, the first and second heated sloped surfaces inclined downwardly towards each other from an upper end to a lower end of the heated sloped surfaces;
      a passage defined between the lower ends of the heated sloped surfaces, through which melted polymer may drain, the first and second heated sloped plates each having one or more heating elements therein, wherein the volume of the heating element increases in the first and second heated sloped plates towards the lower end of the heated sloped surfaces such that the temperature profile of the first and second heated sloped surfaces increases towards the passage;
   a receiving zone having a receiver disposed below the passage for receipt of melted polymeric textile product from the passage; and
   a housing enclosing the heating zone and receiving zone;
   introducing the polymeric textile into the heating zone so the polymeric textile product comes into contact with the first and/or second heated sloped surfaces;
   maintaining the temperature profile in a predetermined range with the temperature increasing from the upper end to the lower end such that a predetermined inclination of the first and second heated sloped surfaces in combination with a predetermined temperature profile melts the polymeric textile product without straightening out the molecular orientation of the polymeric textile product and moves the melted polymeric textile product towards the lower end by achieving a tumbling effect; and
   collecting the melted polymeric textile product in the receiver.

2. The method of claim 1, further comprising a step of providing another heating element for supplying heat to the receiver.

3. The method of claim 1, further comprising a step of providing a cooling arrangement for cooling the receiver.

4. The method of claim 1, further comprising a step of providing an integrated heating element and cooling arrangement to provide an optional heating or cooling surface for heating or cooling the receiver.

5. The method of claim 1, wherein the step of providing the compacting apparatus further comprise providing the passage having a longitudinal length and a width, where the width is in the range of 15 mm to 75 mm.

6. The method of claim 1, wherein the step of providing the compacting apparatus further comprise providing a cooling zone remote from the heating zone and a transfer arrangement for transferring the receiver to the cooling zone.

7. The method of claim 1, wherein the step of providing the compacting apparatus further comprise inclining the first sloped surface at less than 45 degrees to a vertical axis, and/or inclining the second heated sloped surface at less than 45 degrees to a vertical axis.

8. The method of claim 7, wherein the first heated sloped surface is inclined to the vertical axis of between 25 degrees and less than 45 degrees, and/or wherein the second heated sloped surface is inclined to the vertical axis between 25 degrees and less than 45 degrees.

9. The method of claim 1, wherein the step of providing the compacting apparatus further comprise inclining the first sloped surface at an angle of between 25 and 45 degrees to a vertical axis and/or inclining the second heated sloped surface at an angle of between 25 and 45 degrees to a vertical axis.

10. The method of claim 1, wherein the step of maintaining the temperature profile further comprise arranging the first and/or second heated sloped surfaces for being heated to the predetermined temperature range of 250° C. to 310° C.

11. The method of claim 1, wherein the step of providing the compacting apparatus further comprise providing an insulation material at the lower end(s) of the first and/or second heated sloped surfaces for reducing the rate of cooling of the first and/or second heated sloped surfaces.

12. The method of claim 1, wherein the step of providing the compacting apparatus further comprise providing a coating on the first and/or the second heated sloped surfaces to assist transfer of material thereover.

13. The method of claim 1, wherein the step of providing the compacting apparatus further comprise providing a monitoring and recording arrangement for monitoring and recording first and/or second heated sloped surface temperatures and/or dwell time of melted polymer transferred through the passage.

14. The method of claim 1, wherein the compacting apparatus further comprise a filter arrangement and a condenser arrangement, the housing being in fluid communication with the filter arrangement for filtering gases received from the housing and the condenser is positioned intermediate the housing and the filter arrangement.

15. The method of claim 1, wherein the step of maintaining the temperature profile further comprise arranging the first and/or second heated sloped surfaces for being heated to the predetermined temperature range of 275° C. to 295° C.

16. The method of claim 1, wherein the step of maintaining the temperature profile further comprise arranging the first and/or second heated sloped surfaces for being heated to the temperature at substantially 285° C.

17. The method of claim 1, wherein the opposing first and second heated sloped plates of the compacting apparatus are a generally flat plate.

18. The method of claim 1, wherein the inclined angles of the opposing first and second heated sloped plates are different.

19. The method of claim 1, wherein the predetermined range of the first and/or second heated sloped surfaces changes between substantially 260° C. at the upper end to substantially 295° C. at an edge adjacent to the passage.

* * * * *